United States Patent
Oku et al.

[19]

[11] Patent Number: 6,106,778
[45] Date of Patent: Aug. 22, 2000

[54] BLOOD CELL COUNT/IMMUNOASSAY APPARATUS USING WHOLE BLOOD

[75] Inventors: Narihiro Oku; Yasuo Yamao, both of Miyanohigashi-machi, Japan

[73] Assignee: Horiba, Ltd., Kyoto, Japan

[21] Appl. No.: 09/161,127

[22] Filed: Sep. 25, 1998

[30] Foreign Application Priority Data

Sep. 27, 1997 [JP] Japan ...................................... 9-279963
Oct. 4, 1997 [JP] Japan ...................................... 9-287729

[51] Int. Cl.[7] ......................... G01N 25/20; G01N 21/20; G01N 33/48; G05B 1/00; B01J 19/08
[52] U.S. Cl. ............................. 422/50; 422/55; 422/58; 422/63; 422/67; 422/68.1; 422/73; 422/82.05; 422/81; 422/99; 422/102; 422/103; 422/105; 422/108; 422/119; 422/187; 422/188; 422/189; 422/190; 422/192; 422/193; 422/224; 422/225; 422/236; 436/43; 436/63; 436/164; 436/174; 436/175; 436/179; 436/180; 436/518; 436/522; 436/523; 436/805
[58] Field of Search ................................. 422/50, 55, 58, 422/63, 67, 68.1, 73, 82.05, 81, 99, 102, 103, 105, 108, 119, 187, 188, 189, 190, 192, 193, 224, 225, 236; 436/43, 63, 164, 174, 179, 175, 180, 518, 522, 523, 805

[56] References Cited

U.S. PATENT DOCUMENTS

| | | |
|---|---|---|
| 3,689,632 | 9/1972 | Mizushima et al. . |
| 3,944,791 | 3/1976 | Baxter, Jr. .................................. 235/92 |
| 4,030,888 | 6/1977 | Yamamoto et al. ....................... 23/253 |
| 4,251,768 | 2/1981 | Angel et al. ............................... 324/71 |
| 4,379,847 | 4/1983 | Fruitstone et al. . |
| 4,558,947 | 12/1985 | Wardlaw .................................... 356/39 |
| 4,653,078 | 3/1987 | Aritomi et al. ........................... 377/10 |
| 4,683,579 | 7/1987 | Wardlaw .................................... 377/11 |
| 4,745,279 | 5/1988 | Karkar et al. ........................... 250/343 |
| 4,822,568 | 4/1989 | Tomita ....................................... 422/73 |
| 4,883,765 | 11/1989 | Tamir et al. .............................. 436/71 |
| 4,889,815 | 12/1989 | Bradwell et al. . |

(List continued on next page.)

FOREIGN PATENT DOCUMENTS

| | | |
|---|---|---|
| 0367475 | 5/1990 | European Pat. Off. . |
| 409606 | 11/1991 | European Pat. Off. . |
| 57-150382 | 9/1982 | Japan . |
| 60-244861 | 12/1985 | Japan . |
| 7035752 | 2/1995 | Japan . |
| 8505640 | 12/1985 | WIPO . |

OTHER PUBLICATIONS

Abstract, "Production of Food Colourant for Marking Meat Portions . . . ," by T.P. Perkel et la., Derwent Publishing, Feb. 9, 1995.

*Primary Examiner*—Christopher L. Chin
*Assistant Examiner*—Pensee T. Do
*Attorney, Agent, or Firm*—Price, Gess & Ubell

[57] ABSTRACT

A compact combination blood cell count and immunoassay apparatus for measuring drawn whole blood specimen includes a load station for receiving the whole blood specimen and a nozzle member that can selectively withdraw whole blood from the blood specimen. A blood cell count section and an immunoassay section are mounted along a unitary path of movement of the nozzle member so that a single nozzle member may be used for transporting the whole blood to the respective blood cell count section and immunoassay section. A controller can automatically direct a transport mechanism to use only the whole blood and to perform various steps of adding dilution liquid and reagents, along with appropriate washing of the nozzle and sample cells to insure an automatic operation. A hematozorit value can be determined from the blood cell count signal and used to correct the immunoassay signal when whole blood is used.

16 Claims, 6 Drawing Sheets

U.S. PATENT DOCUMENTS

| | | |
|---|---|---|
| 4,997,769 | 3/1991 | Lundsgaard . |
| 5,019,351 | 5/1991 | Schulz ........................................ 422/99 |
| 5,041,266 | 8/1991 | Fox ......................................... 422/102 |
| 5,043,289 | 8/1991 | Serres . |
| 5,132,087 | 7/1992 | Manion et al. ........................... 422/58 |
| 5,372,136 | 12/1994 | Steuer et al. ............................ 128/633 |
| 5,380,491 | 1/1995 | Carver, Jr. et al. ...................... 422/73 |
| 5,541,117 | 7/1996 | Karl et al. . |
| 5,555,198 | 9/1996 | Asano . |
| 5,611,997 | 3/1997 | Langley et al. ........................... 422/73 |
| 5,665,312 | 9/1997 | Sperber et al. ........................... 422/81 |
| 5,728,351 | 3/1998 | Carver, Jr. ................................ 422/73 |
| 5,731,206 | 3/1998 | Ledis et al. . |
| 5,830,639 | 11/1998 | Levine et al. .............................. 435/4 |
| 5,916,814 | 6/1999 | Kenney .................................... 436/70 |
| 5,939,326 | 8/1999 | Chupp et al. ............................. 436/43 |
| 6,030,845 | 2/2000 | Yamao et al. . |

BLOOD CELL COUNT/IMMUNOASSAY APPARATUS USING WHOLE BLOOD

BACKGROUND OF THE INVENTION

1. Field of the Invention

The present invention relates to a combination blood cell count/immunoassay apparatus capable of operating with whole whole blood to provide multiple measurements in an efficient manner.

2. Description of Related Art

It has been known to use an inflammation marker as a technique for observing any sign of inflammation occurring in a human body, including its degree and its progress. For a typical inflammation marker, examples include a count of the number of white blood cells, erythrocyte sedimentation rate, acute phase protein, serum protein fractional value, serum sialic acid, etc., and these are measured in various combinations and the results are utilized for diagnosis of inflammation. Of these examples, particularly, the measurement of the number of white blood cells and C-reactive protein (CRP), acute phase protein, is effective for diagnosis of inflammation and infectious diseases, but there is no known apparatus which can measure both simultaneously, and the former is usually measured by a blood cell counter and the latter by an immunoassay apparatus, respectively.

However, when measurements are carried out individually using the blood cell counter and the immunoassay apparatus, the samples used for measurements are the whole blood for the former and primarily blood serum for the latter. When the whole blood is obtained as a sample, the blood must be both drawn with an anticoagulant and without an anticoagulant, respectively, while the serum needs time to wait for blood coagulation and centrifuge, accordingly, the above technique is not suited for those medical facilities where a professional laboratory engineer or technician is unable to be constantly in attendance, such as small doctor's offices and clinics, clinics in remote areas, holiday clinics, emergency laboratory, etc.

There is also known an immunoassay apparatus which can carry out a measurement with whole blood, but when the whole blood is used for samples, if the targeted immunoassay item does not exist in the blood cell and only exists in serum or plasma, and errors arising from variations in hematocrit, which has comparatively large individual differences, are generated.

Thus, the prior art is still seeking to provide an improved blood cell count and immunoassay apparatus.

SUMMARY OF THE INVENTION

In view of the foregoing, it is one of the objects of this invention to provide a blood cell count/immunoassay apparatus capable of using whole blood to obtain data on both a complete blood cell count and also immunity items in a simultaneous manner.

It is another object of this invention to provide a blood cell count/immunoassay apparatus capable of using whole blood which has a relatively simple mechanism for sampling specimens and reagents and at the same time is easy to handle.

In order to achieve the above objects, the blood cell count/immunoassay apparatus using whole blood according to this invention comprises an immunoassay section for measuring immunity and a blood cell measuring section for counting the number of blood cells, wherein the same drawn whole blood sample is used in both measuring sections and at the same time, and the results of immunoassay are corrected using a hematocrit value obtained by the measurement of the number of blood cells.

In this embodiment of the invention, it is preferable to carry out a blood cell count in a blood cell measuring section while immunity reactions are allowed to take place in an immunoassay section. According to this first embodiment, since the blood cell count and immunity item measurement can be simultaneously carried out with whole blood, samples that must be handled are whole blood only and there is no need for a serum separation step, and accordingly measurement can be undertaken in a short time after blood is drawn from the patient, and at the same time, a person who is not a professional laboratory technician can measure the results easily. Consequently, this is particularly useful for both emergency and early diagnosis of inflammation and infectious diseases, and at the same time, a required inspection can be carried out even in small doctors' offices and clinics, clinics in remote areas, holiday clinics, emergency laboratories, etc.

The actual hardware components of a probe unit section, processor/controller, display and output units, etc., can be used for both a blood cell count and an immunoassay, and the cost of the equipment can be reduced as compared to conventional apparatus in which such units must be equipped individually. The measurements can be coordinated by the processor/controller to provide an automatic instrument.

The blood cell count/immunoassay apparatus using whole blood according to this second embodiment has an immunoassay section for immunoassay, a container for containing reagents used for immunoassay, and a blood cell count section for counting the blood cells are consecutively positioned or arranged in a straight line or an arc, so that with only one sampling nozzle, specimens and reagents can be sampled and mixed.

In a second embodiment, it is preferable to use a sample cell of the blood cell count section also as a waste liquid chamber for cleaning the sampling nozzle. According to this second embodiment, because the mechanism for sampling reagents, etc. becomes simplified, and less component parts are required, there is less of a chance for experiencing trouble during measurement, and at the same time cost can be reduced. When the sample cell of the blood cell count section is also used as a waste liquid chamber for cleaning the sampling nozzle, the amount of dedicated waste liquid and cost reduction is promoted.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide a blood cell count/immunoassay apparatus using whole blood for both an immunoassay and blood cell count and method.

Referring now to FIGS. 1–6, preferred embodiments of this invention will be described in detail hereinafter.

Figure 1:
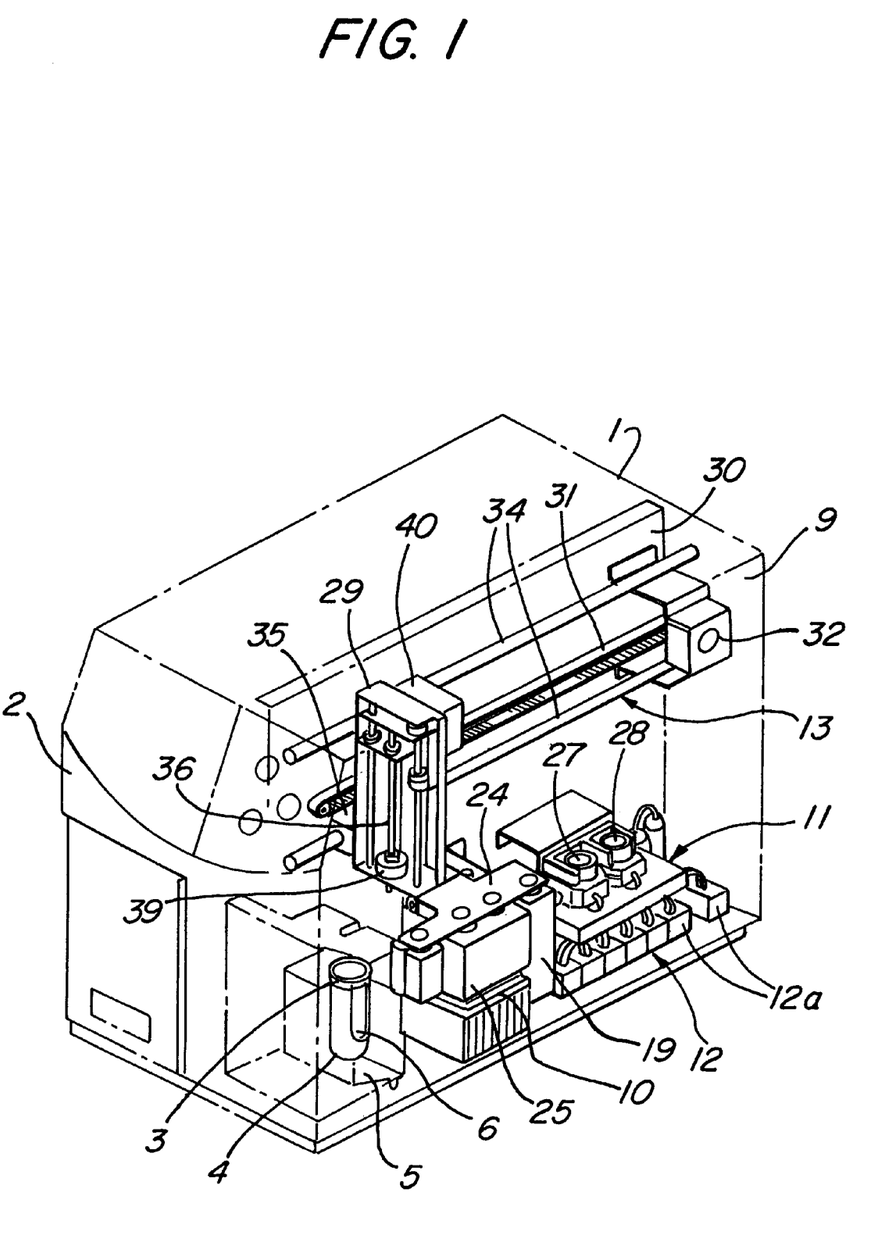
FIG. 1 is a perspective view of one example of a blood cell count/immunoassay apparatus using whole blood according to this invention with a side panel removed.
Figure 2:
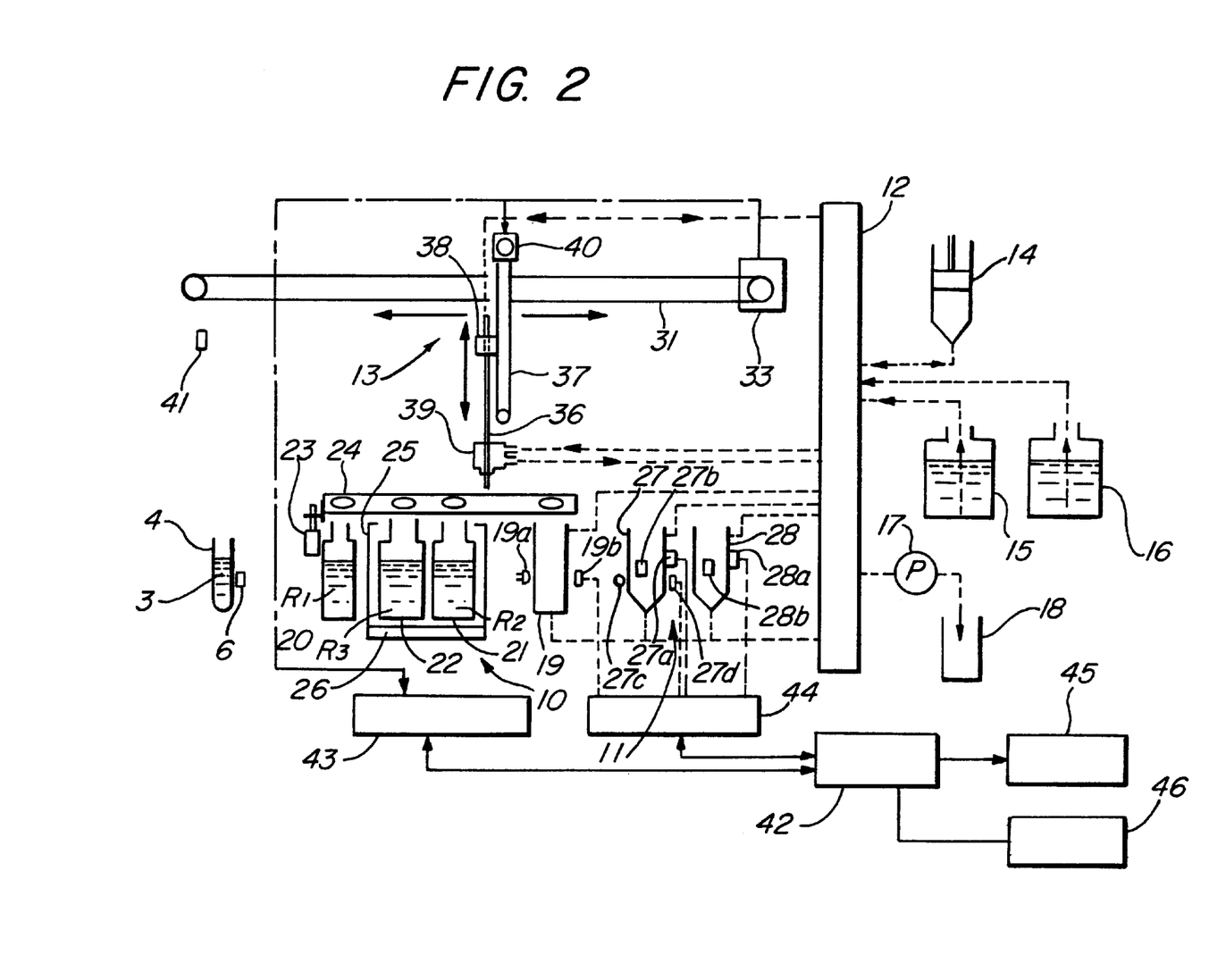
FIG. 2 is a drawing schematically showing the overall configuration of the blood cell/immunoassay apparatus using whole blood.
Figure 3:
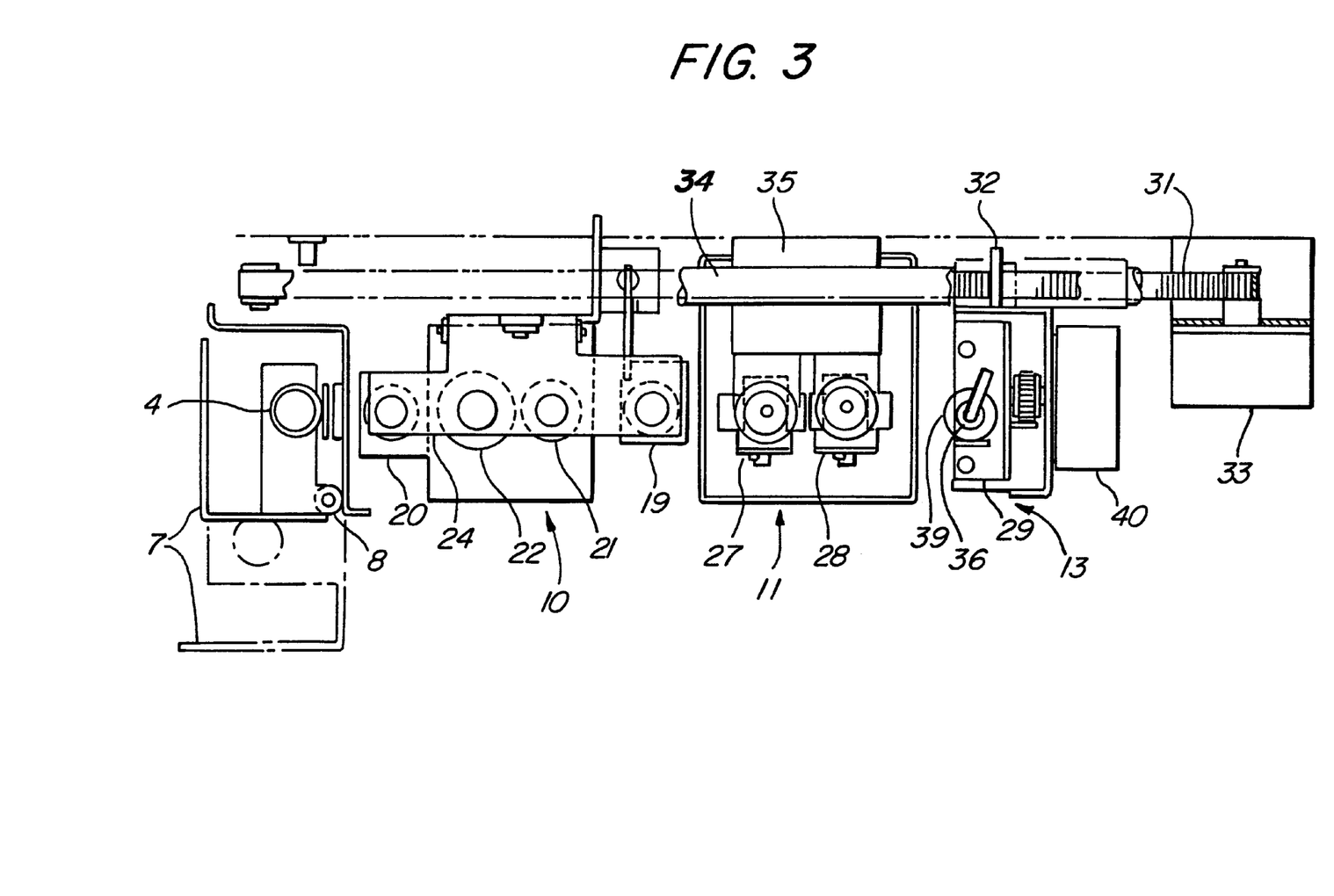
FIG. 3 is a view as seen from above of the principal portion of the blood cell count/immunoassay apparatus using whole blood.

FIG. 1 is a perspective view showing one example of a blood cell count/immunoassay apparatus using drawn whole blood according to this invention with the housing side panel removed. FIG. 2 is a drawing schematically showing the overall configuration of the blood cell count/immunoassay apparatus using whole blood. FIG. 3 is a view as seen from above of the principal portion of the blood cell count/immunoassay apparatus using whole blood. In these drawings, numeral 1 is an apparatus case, and on the side of a front portion 2 of the case, a specimen setting section load station 5 for setting a specimen container 4, containing whole blood 3 as a specimen, is formed in an operative condition in a section of the housing recessed inward. Numeral 6 is a measuring key provided in this specimen setting section 5, and 7 is a door or closure member which swings in the direction of both arrow marks of FIG. 3 with a hinge 8 at the center and opens and closes the specimen setting section 5.

Below a side surface portion 9 of the apparatus case 1, an immunoassay section 10 for carrying out immunoassay and a blood cell count section 11 for carrying out a blood cell count are arranged along a straight line as seen from the front side in order of the side closest to the front portion 2, and at the same time, a solenoid valve section 12 comprising a plurality of solenoid valves 12a is installed as a bank of valves that can be automatically opened and shut in correlation with the measurement procedures. Above the side surface portion 9, a probe unit section 13 as a sampling mechanism can move linearly above the immunoassay section 10 and the blood cell count section 11 in a unitary or horizontal straight line between the specimen setting section 5 and the blood cell count section 11 while being automatically lowered and raised vertically at the selected stations for the particular measurement procedure.

In FIG. 2, numeral 4 is a fixed-rate injector, 15 is a dilution liquid container, 16 is a hemolysis reagent container, and 17 is a pump, and these components 15 through 17 are connected to the solenoid section 12. Numeral 18 is a waste liquid container connected to the pump 17.

Now, the configuration of the immunoassay section 10, blood cell count section 11, and the probe unit section 11 is described in detail. First of all, the immunoassay section 10 is configured to measure a C-reactive protein, CRP in this embodiment. That is, in FIG. 2, numeral 19 is a cell for measuring CRP (hereinafter called the "CRP cell"), which is configured to be equipped with a light irradiating section 19a and a light detection section 19b, as well as to properly agitate the sample liquid contained inside as known in the industry. Numerals 20, 21, 22 are containers containing reagents used for CRP measurement, in which a hemolysis reagent (hereinafter called the "R1 reagent"), a buffer solution (hereinafter called the "R2 reagent"), and an anti-human CRP sensitized latex immunoreagent (hereinafter called the "R3 reagent") are contained, respectively.

The CRP cell 19 and reagent containers 20 through 22 are arranged in one straight line with respect to the load or setting position of the specimen container 4 of the specimen setting section 5, and these components 19 through 22 are configured to be opened and closed in group by a cover 24 which is powered to swing vertically upward by a solenoid 23. Numeral 25 is a cooler box equipped with an electronic cooler 26 comprising, for example, a Peltier element, and in the illustrated example, reagents R2, R3 are contained in the cooler box 26.

Next, the blood cell count section 11 is configured to measure WBC (white blood cell count), RBC (red blood cell count), PLT (number of platelets), MCV (mean corpuscular volume), and Hct (hematocrit) by an electric resistance method and Hgb (hemoglobin concentration) by an absorptiometric method in an cyanmethemoglogin method, respectively. That is, in FIG. 2, numeral 27 is a WBC/Hgb blood cell count cell (hereinafter called simply the "WBC cell") and is equipped with measuring electrodes 27a, 27b for measuring WBC and a light irradiation section 27c and light receiving section 27d for measuring Hgb. Numeral 28 is an RBC/PLT blood cell count measuring cell (hereinafter called simply an "RBC cell"), and is equipped with measuring electrodes 28a, 28b for measuring RBC and PLT. These cells 27, 28 are arranged to form one straight line together with the CRP cell 19 and reagent containers 20–22 in the CRP measuring section 10, as shown in FIG. 3. The WBC cell 27 serves also as a waste liquid chamber for cleaning the sampling nozzle 36, to be discussed later.

In addition, the probe unit section 13 is, for example, configured as shown in FIGS. 1 and 2, where numeral 29 is a nozzle unit, and with suitable connecting members 32, this nozzle unit 29 is fixed to a timing belt 31 installed horizontally along the base member 30 above the immunoassay section 10 and the blood cell count section 11. The nozzle unit is configured in a vertical alignment and can reciprocate along the horizontal direction. More specifically, the nozzle unit 29 is configured to reciprocate nearly right above the immunoassay section 10, containers containing reagents used for immunoassay, devices 18–20, and the blood cell count section 11 placed in one straight line. Numeral 33 is a motor for driving a timing belt 31, numeral 34 is a pair of guide members for guiding the guided member 35 installed through the nozzle unit 29, and these components are mounted to the base member 30 via a suitable member.

Numeral 36 is a sampling nozzle, which is mounted to a nozzle holder 38 that can be moved vertically by a second timing belt 37 provided in the nozzle unit 29. The top end side (bottom end side) of this sampling nozzle 36 is configured to be inserted through a sampling nozzle washer 39 to allow the outer circumference of the top end portion to be washed. Numeral 40 is a motor for driving the timing belt 37. Numeral 41 is a sensor to detect whether the sampling nozzle 36 is located at a home position or not to thereby enable the sequence of movements for an automatic measuring procedure.

In FIG. 2, numeral 42 is a microcomputer (MCU) which functions as a controller and processor for comprehensively controlling all the sections of the apparatus in an automatic fashion as well as performing various arithmetic computations using outputs from the CRP measuring section 10 and the blood cell count section 11. Numeral 43 is a driver for transmitting driving signals to the solenoid valve section 12, motors 33, 40 of the probe unit section 13, etc. based on the commands from MCU 42. 44 is a signal processor for processing and transmitting output signals from the CRP measuring section 10 and the blood cell count section 11 to MCU 42. 45 is an apparatus for displaying the results, etc., for example, a color display unit, processed and obtained in MCU 42, and 46 is a printer as an output unit.

In FIG. 2, dotted lines show flows of specimen 3 or various reagents, and slightly thick alternate long and short dash lines show flows of control signals, and the thin alternate long and short dash lines show flows of signals obtained by the measurement.

Figure 4:
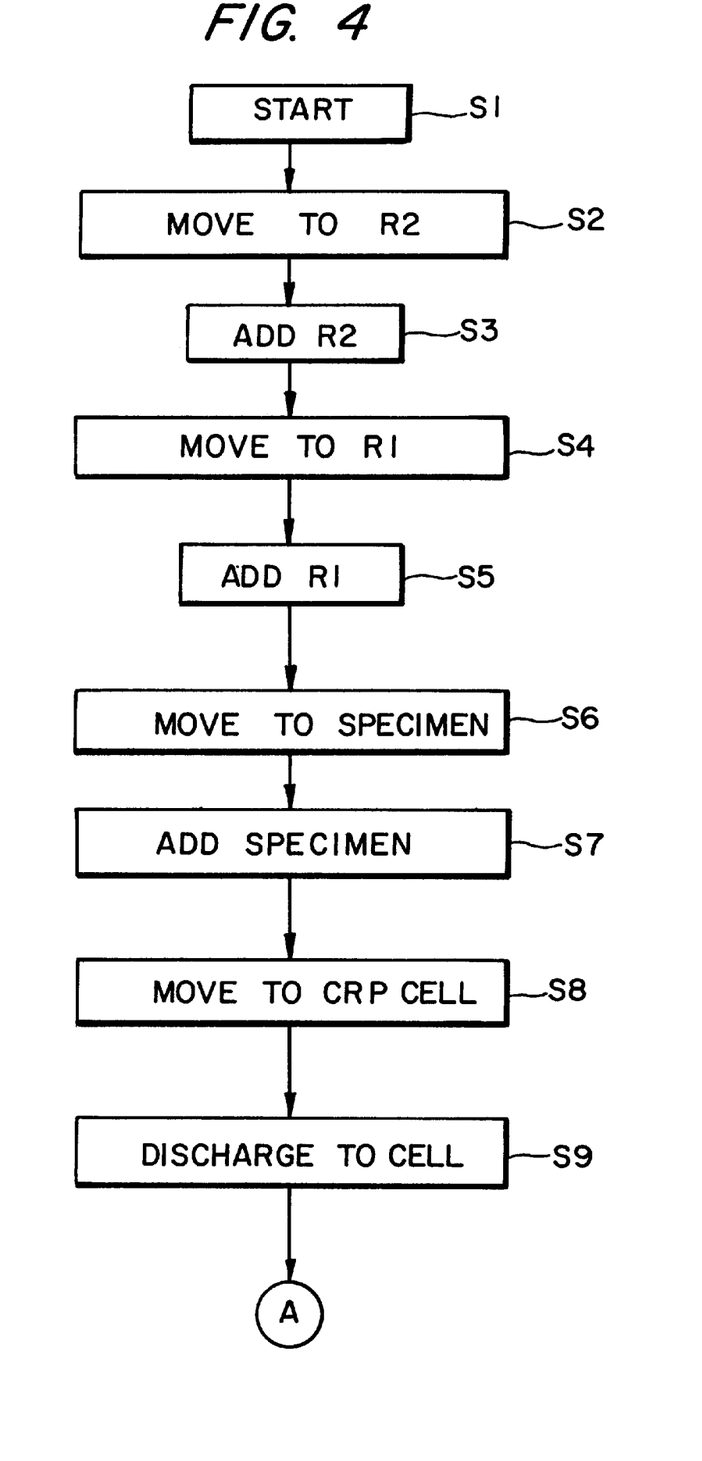
FIG. 4 is a flow chart showing one example of a measuring procedure.
Figure 5:
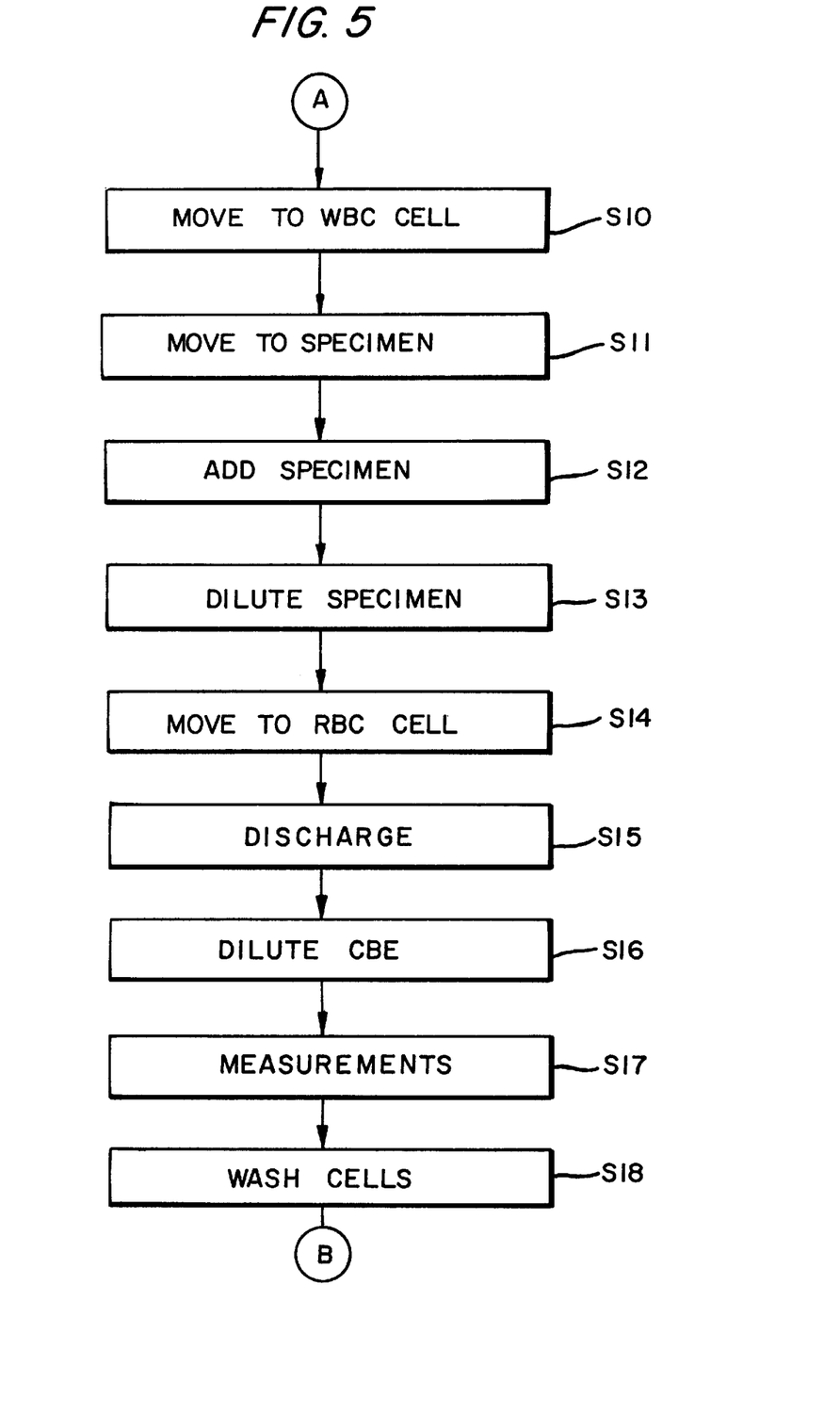
FIG. 5 is a flow chart following the portion shown in FIG. 4.
Figure 6:
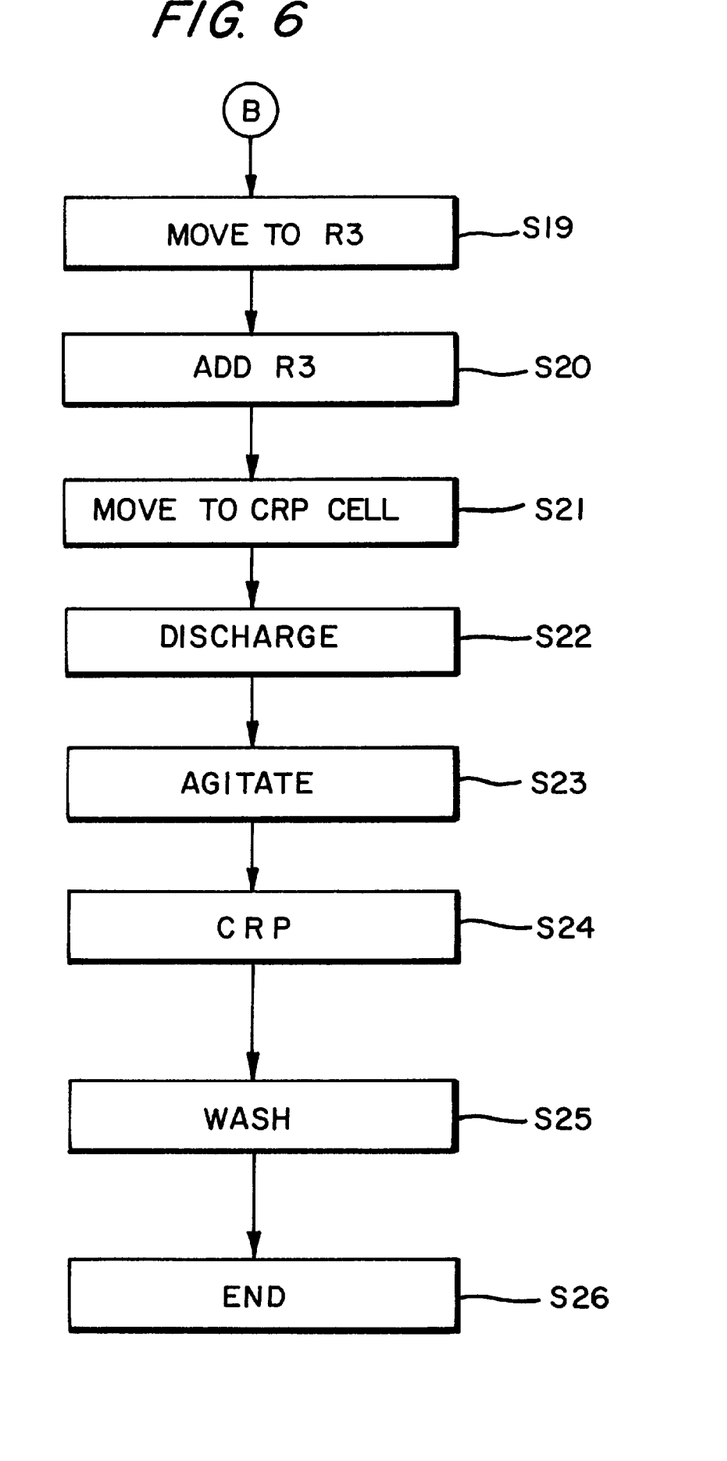
FIG. 6 is a flow chart following the portion shown in FIG. 5.

Referring to FIGS. 4 through 6, in which one example of a measuring procedure is shown, the operation of the blood cell count/immunoassay apparatus using whole blood of the above configuration is described. When the measuring key 6 (Step S1) is turned on, the sampling nozzle 36, located at the home position, moves to the R2 reagent position (Step S2) and sucks the R2 reagent (Step S3). If not at the home position it is driven to the home position to be detected by the sensor 41 to enable the procedure. After sucking up this reagent, the sampling nozzle 36 moves upward, and the outer surface is then automatically washed with a dilution liquid as a washing liquid supplied to the sampling nozzle washer 39. Thereafter, the sampling nozzle 36 returns to the R2 reagent position.

Then, the sampling nozzle 36 moves to the R1 reagent position (Step S4) and sucks the R1 reagent (Step S5). After sucking this reagent, the sampling nozzle 36 moves upwards, and the outer surface is again automatically washed with the dilution liquid as a washing liquid is supplied to the sampling nozzle washer 39. Thereafter, the sampling nozzle 36 returns to the R1 reagent position.

The sampling nozzle 36 further moves to the specimen setting position (Step S6) and sucks up the specimen (whole blood) 3 into the specimen container 4 for CRP measurement (Step S7). After sucking up this specimen, the sampling nozzle 36 moves upwards, and the outer surface is again washed with the dilution liquid as a washing liquid supplied to the sampling nozzle washer 39. Thereafter, the sampling nozzle 36 returns to the specimen 3 position.

The sampling nozzle 36 moves to the CRP cell 19 (Step S8) and discharges the specimen 3, R1 reagent, and R2 reagent into the CRP cell 19 (Step S9).

The sampling nozzle 36, after discharging, moves to the WBC cell 27 position (Step S10), and discharges the specimen 3, R1 reagent, and R2 reagent into the WBC cell 27 together with dilution liquid supplied by the pump 17.

The sampling nozzle 36 again has its outer surface washed with the dilution liquid as a washing liquid supplied to the sampling nozzle washer 39. The waste liquid in this washing is received by the WBC cell 27 and is discharged to the waste liquid container 18 by the pump 17. Again, supplying the dilution liquid to the WBC cell 27 by the sampling nozzle washer 39 and discharging it to the waste liquid container 18 by the pump 17, the WBC cell 27 is washed. By the way, the waste liquid may be also received in the RBC cell 28.

The sampling nozzle 36, when finished with the washing, moves to the specimen setting position (Step S11) and sucks up the specimen 3 in the specimen container 4 for CBC measurement (Step S12). After sucking up this specimen, the sampling nozzle 36 moves upwards and has the outer surface washed with the dilution liquid as the washing liquid is supplied to the sampling nozzle washer 39.

The sampling nozzle 36, when finished with the washing, discharges the specimen 3 into the WBC cell 27, while the dilution liquid in the dilution liquid container 15 is injected, in a specified amount, into the WBC cell 27 via the solenoid section 12, and a primary dilution of the CBC specimen takes place (Step S13).

The sampling nozzle 36, located at the WBC cell 27 position, sucks up a specified amount of primary-diluted CBC specimen, moves to the RBC cell 28 (Step S14), and discharges the primary-diluted CBC specimen sucked into this cell 28 (Step S15), while the dilution liquid in the dilution liquid container 13 is injected in a specified amount into the RBC cell 26 via the solenoid section 10, and a secondary dilution of the CBC specimen takes place (Step S16).

After completion of the primary and secondary dilution, the hemolysis chemical in the hemolysis chemical container 16 is injected in a specified amount into the WBC cell 27 via the solenoid valve section 12, and WBC and Hgb measurements are carried out (Step S17), and the data at that time is taken into MCU 42 vial the signal processor 44. When the above measurements are completed, the WBC cell 27 and the RBC cell 28 are washed with the dilution liquid (Step S18).

As described above, in Steps S10–S28, a CBC measurement is carried out in the blood cell count section 1, but during this period (about 60 seconds), in the CRP cell 19 hemolysis reactions take place between the specimen 3, R1 reagent, and R2 reagent and at the same time the interfering substance is removed.

And when the CBC measurement is completed, the sampling nozzle 36, located at the RBC cell 28 position, moves to the WBC cell 27 position, and the inner surface of the WBC cell 27 is washed with the dilution liquid supplied by the pump 17, while the outer surface is washed with the dilution liquid as the washing liquid supplied to the sampling nozzle washer 39. The waste liquid at this time is received into the WBC cell 27 and discharged to the waste liquid container 18 by the pump 17. And again, by supplying the dilution liquid to the WBC cell 27 with the sampling nozzle washer 39 and discharging it to the waste liquid container 18 by the pump 17, the WBC cell 27 is washed. Thereafter, the sampling nozzle 36 moves to the R3 reagent position (Step S19) and sucks up the R3 reagent (Step S20), and the R3 reagent is mixed in the reaction liquid of the specimen 3, R1 reagent, and R2 reagent.

After discharging the R3 reagent, the sampling nozzle 36 moves to the WBC cell 27 position and washes the WBC cell 27 inner surface with the dilution liquid supplied by the pump 17, and the outer surface is washed with the dilution liquid with the washing liquid supplied to the sampling nozzle washer 39. The waste water in this event is received by the WBC cell 27 and discharged into the waste liquid container 18 by the pump 17. Again, by supplying the dilution liquid to the WBC cell 27 with the sampling nozzle washer 39 and discharging it to the waste liquid container 18 by the pump 17, the WBC cell 27 is also washed.

The liquid is thoroughly agitated in the CRP cell 19 (Step S23), immunoreaction is generated, and a CRP measurement is carried out (Step S24), and the data in such an event is taken into MCU 42 via the signal processor 44. Upon completion of the measurement, the CRP cell 19 is washed with the dilution liquid (Step S25), and all the measurements are finished (Step S26).

In the MCU 42, based on the data obtained by the CBC measurement carried out in the blood cell count section 11 and pre-stored known program values and algorithms, measurements such as RBC (red blood cell count) and mean corpuscular volume (MCV), etc. are obtained. In the MCU 42, based on the data obtained by the CRP measurement carried out at the CRP measuring section 10, changes of absorbency per specified time is obtained, and the CRP concentration in whole blood is obtained from a pre-stored calibration curve determined in advance from serum (or plasma) of a known concentration.

In such an event, because with respect to the CRP measurement, the whole blood with anticoagulant added is used for the specimen 3 as in the case of the CBC measurement, a plasma component volume error which is generated by the use of the whole blood must be corrected. Therefore, the hematocrit (Hct) is found from RBC (red blood cell) and red blood cell volume (RCV), and using this hematocrit, the CRP concentration in the whole blood obtained by the CRP measurement is further corrected by the following correction formula, and the CRP concentration in the plasma is therefor accurately determined.

That is, let A denote the CRP concentration in whole blood and B the hematocrit, the CRP concentration C in the plasma can be found by the following expression:

$$C = A \times 100/(100-B)$$

While each of the measurements obtained by the MCU 42 are stored in memory, for example, in a storage built in the MCU 41, they can be displayed on the display unit 45 by items or outputted by a printer 46.

In the blood cell count/immunoassay apparatus using whole blood, the blood cell is counted at the CBC measuring section 11, while the hemolysis and interfering substance removing reactions are allowed to take place at the CRP measuring section 10, the whole time required for CRP measurement and CBC measurement can be shortened and at the same time, the correction carried out on the results obtained by the CRP measurement by the results obtained by the CBC measurement can be smoothly undertaken.

In the above-mentioned embodiment, the specimen container 4, immunoassay section 10, containers containing reagents used for immunoassay 20–22, and blood cell count section 11 are arranged on one straight line, while the sampling nozzle 36 is located nearly right above and reciprocated linearly, but in place of this, it is possible to arrange the specimen container 4, immunoassay section 10, containers containing reagents used for immunoassay 20–22, and blood cell count section 11 in an arc form, and to locate the sampling nozzle 36 nearly right above and reciprocated it in an arc motion to result in the same operation and effect.

According to the blood cell count/immunoassay apparatus using whole blood according to the first and second embodiments, since the blood cell count and immune items can be measured simultaneously using the whole blood with one apparatus, the whole blood can be used as the specimen, and serum separation is no longer needed, and measurement can be carried out shortly after the blood is drawn. In addition, the specimen and reagents required for blood the cell count and immune item measurements can be supplied to the blood cell count section and immunoassay section with only a single sampling nozzle. Thus, the mechanism for sampling the specimen and reagents can be simplified, and the measurements can be carried out simply and quickly even without a professional laboratory engineer or technician.

Particularly, in the first embodiment, the probe unit section, processor and controller, display and output units, etc. can be used in common by both the blood cell count measurement and immunoassay measurement, and the cost can be reduced for those parts shared by the two measurements, as compared to conventional apparatus in which such units must be equipped individually, and at the same time, the apparatus can be configured in a compact construction.

In the second embodiment, when the cell of the blood cell count section is also used for a waste liquid chamber, a dedicated waste liquid chamber is not required and the construction can be simplified and a cost reduction is possible.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A combination blood cell count and an immunoassay apparatus can measure a drawn whole blood specimen positioned at a load station, comprising a nozzle member for releaseably holding a portion of the whole blood withdrawn from the load station;

means for adding a dilution liquid;

means for adding reagents;

a blood cell count section for providing signals on blood cells;

an immunoassay section for providing signals on immunoassay;

a transport mechanism for moving the nozzle member to the blood cell count section and the immunoassay section;

a controller for directing the transport mechanism to transport the nozzle member to the blood cell count section and immunoassay section and to mix reagents with the whole blood for the immunoassay section and to dilute the whole blood with the dilution liquid for the blood cell count section; and means for determining a hematocrit from a blood cell count signal and correcting the immunoassay signal with the hematocrit.

2. The apparatus of claim 1, wherein the blood cell count is performed in the blood cell count section, while immunoreactions are taking place in the immunoassay section.

3. The apparatus of claim 1, wherein the load station, immunoassay section and blood cell count section are arranged in a straight line beneath the nozzle member.

4. The apparatus of claim 1, wherein a cell in the blood cell count section is also used as a waste liquid chamber for washing the nozzle member.

5. A combination blood cell count and an immunoassay apparatus comprising:

a nozzle member for holding a sample of whole blood;

a blood cell count section for receiving said sample of whole blood from the nozzle member and providing a hematocrit signal;

an immunoassay section for receiving whole blood from the nozzle member and providing an immunoassay signal; and correcting means for correcting the immunoassay signal with the hematocrit signal.

6. The apparatus of claim 5, wherein the blood cell count is performed in the blood cell count section, while immunoreactions are taking place in the immunoassay section.

7. The apparatus of claim 5, wherein the load station, the immunoassay section and the blood cell count section are arranged in a straight line beneath the nozzle member.

8. The apparatus of claim 5, wherein a cell in the blood cell count section is also used as a waste liquid chamber for washing the nozzle member.

9. A compact combination blood cell count and an immunoassay apparatus for measuring drawn whole blood specimen, comprising:

a load station for receiving a whole blood specimen;

a blood cell count section for providing signals on blood cells;

an immunoassay section for providing signals on immunoassay;

a nozzle member for releaseably holding a portion of the whole blood withdrawn from the load station and delivering the whole blood to each of the blood cell count section and the immunoassay section;

a transport mechanism for moving the nozzle member to the blood cell count section and immunoassay section, the transport mechanism providing a unitary path of movement for the nozzle member to reciprocate along in a horizontal direction above the load station, blood cell count section and immunoassay section and to vertically move the nozzle member for operative contact with the load station, blood cell count section and immunoassay section;

a controller for automatically directing the transport mechanism to transport the nozzle member to the blood cell count section and the immunoassay section; and means for determining a hematocrit from a blood cell count signal and correcting the immunoassay signal with the hematocrit.

10. The apparatus of claim 9, wherein the load station, the immunoassay section and the blood cell count section are arranged in a straight line beneath the nozzle member.

11. The apparatus of claim 9, wherein a cell in the blood cell count section is also used as a waste liquid chamber for washing the nozzle member.

12. The apparatus of claim 9, wherein the blood cell count is performed in the blood cell count section, while immunoreactions are taking place in the immunoassay section.

13. A combination blood cell count and an immunoassay apparatus for automatically measuring the properties of a whole blood specimen, comprising:

a load station for receiving a whole blood specimen drawn directly from a patient;

a single nozzle member for releaseably holding a portion of the whole blood withdrawn from the blood specimen located at the load station; means for adding dilution liquid;

means for adding reagents;

a blood cell count section for providing signals on blood cells;

an immunoassay section for providing signals on immunoassay;

a transport mechanism for moving the nozzle member to the blood cell count section and the immunoassay section;

means for repetitively washing the nozzle member along its travels from the load station to respectively the blood cell count section and the immunoassay section;

a controller for automatically directing the transport mechanism to transport the single nozzle member to the blood cell count section and immunoassay section and to mix reagents with the whole blood for the immunoassay section and to dilute the whole blood with a dilution liquid for the blood cell count section and to wash the single nozzle member at predetermined positions during its travel; and means for determining a hematocrit from a blood cell count signal and correcting the immunoassay signal with the hematocrit.

14. The apparatus of claim 13, wherein the blood cell count is performed in the blood cell count section, while immunoreactions are taking place in the immunoassay section.

15. The apparatus of claim 14, wherein the load station, immunoassay section and blood cell count section are arranged in a straight line beneath the nozzle member.

16. The apparatus of claim 15, wherein a cell in the blood cell count section is also used as a waste liquid chamber for washing the nozzle member.

* * * * *